United States Patent [19]

Cowdery et al.

[11] 4,445,511
[45] May 1, 1984

[54] PACER ELECTRODE CONNECTOR ASSEMBLY

[75] Inventors: David Cowdery, East Ballina; John R. Cooper, Five Dock, both of Australia

[73] Assignee: Telectronics Pty. Ltd., Lane Cove, Australia

[21] Appl. No.: 391,519

[22] Filed: Jun. 24, 1982

[51] Int. Cl.³ ............................................. A61M 1/36
[52] U.S. Cl. ................................ 128/419 P; 128/786; 128/419 D
[58] Field of Search .................... 128/419 P, 786, 784, 128/419 E, 419 D

[56] References Cited

U.S. PATENT DOCUMENTS

| | | | |
|---|---|---|---|
| 3,735,766 | 5/1973 | Bowers et al. | 128/419 P |
| 3,760,332 | 9/1973 | Berkovits et al. | 339/66 R |
| 3,788,329 | 1/1974 | Friedman | 128/419 P X |
| 4,180,078 | 12/1979 | Anderson | 128/419 P |
| 4,182,345 | 1/1980 | Grose | 128/419 P |
| 4,198,991 | 4/1980 | Harris | 128/419 P |
| 4,202,592 | 5/1980 | Rullier et al. | 128/419 P |
| 4,226,244 | 10/1980 | Coury et al. | 128/419 P |
| 4,236,525 | 12/1980 | Sluetz et al. | 128/419 P |

*Primary Examiner*—Edward M. Coven
*Attorney, Agent, or Firm*—Gottlieb, Rackman & Reisman

[57] ABSTRACT

A heart pacer connector assembly for two bipolar electrode lead proximal terminations, each having a forward pin contact and a rearward annular ring contact. Two in-line pairs of metallic termination blocks are connected by four wires to respective lead-through terminals. At least two fluid-insulating, metal-free plastic parts (molded without embedding termination blocks in them) are then slid on the assembly to insulate the termination blocks and to provide a pair of insertion bores for the proximal terminations. The plastic parts are shaped to lock onto capped studs provided on the case, and the plastic parts are sealed to each other. Each termination block for an annular ring contact may consist of a simple hollow cylinder having three equally spaced circumferential cuts, with a contact wire being wrapped around the cylinder, sitting in the cuts and extending into the cylinder bore, and being connected directly to the respective terminal.

37 Claims, 19 Drawing Figures

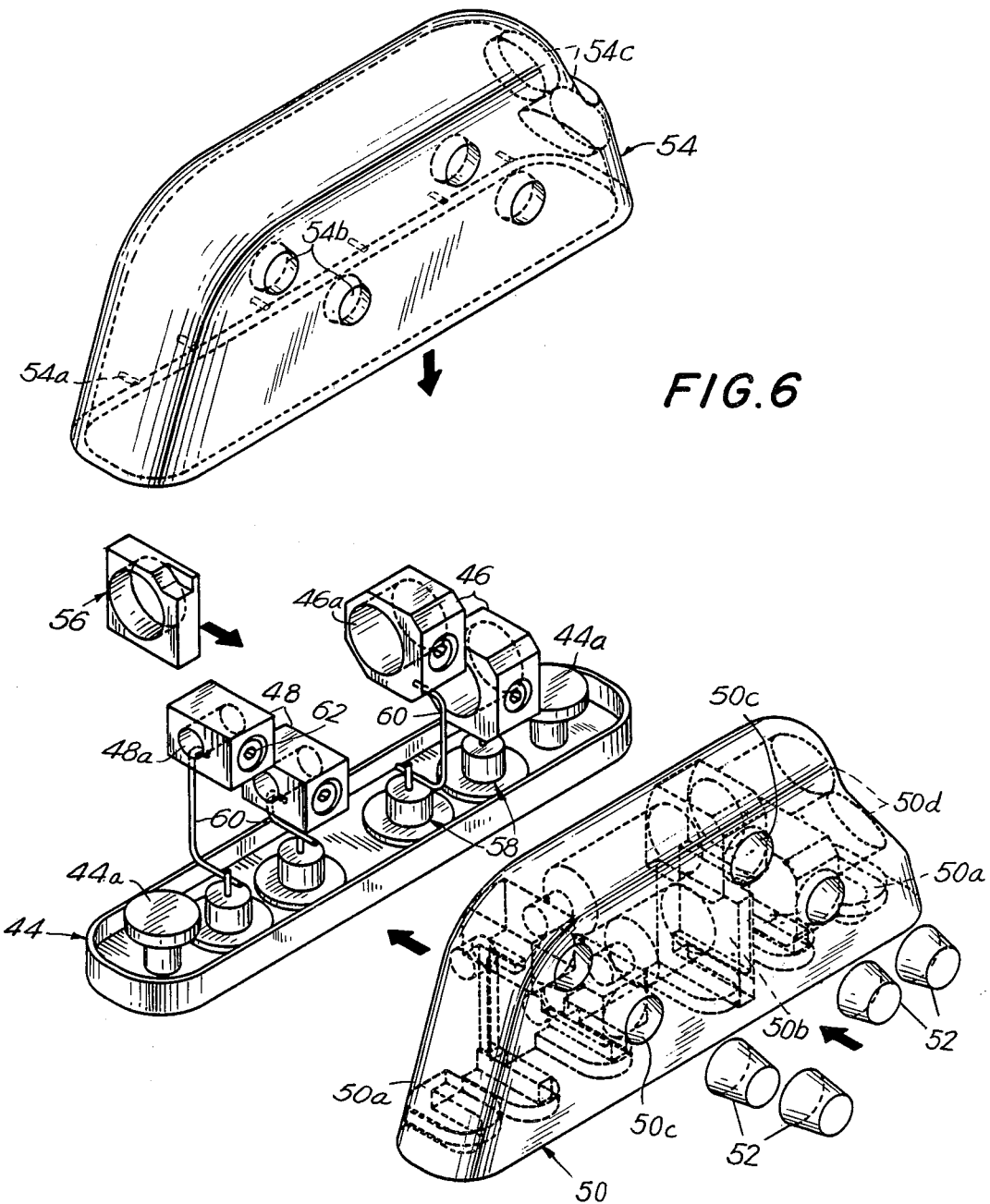

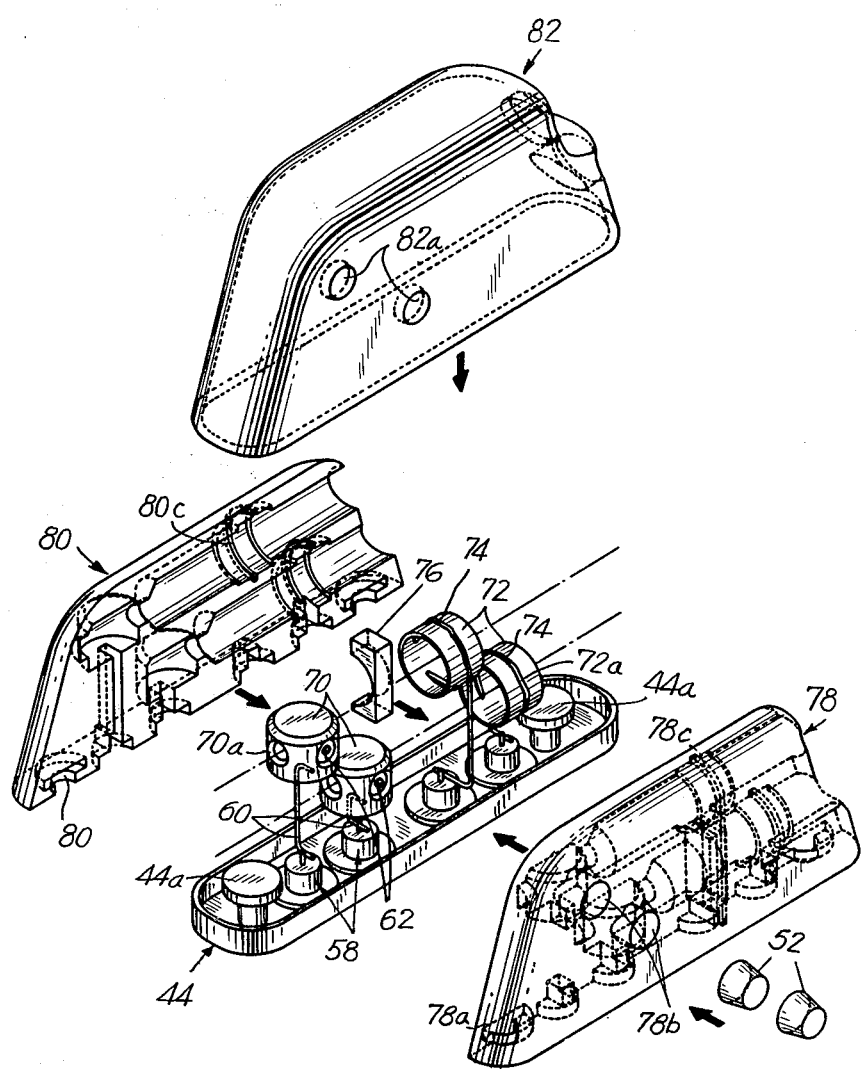

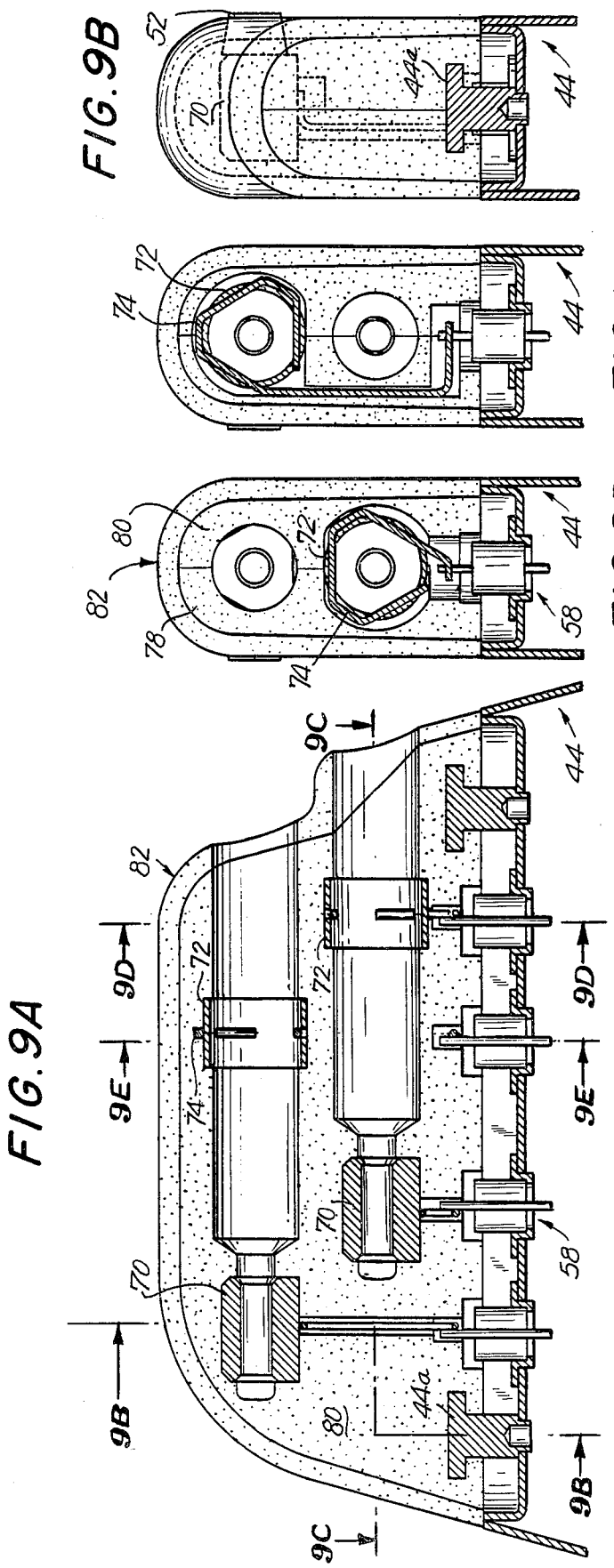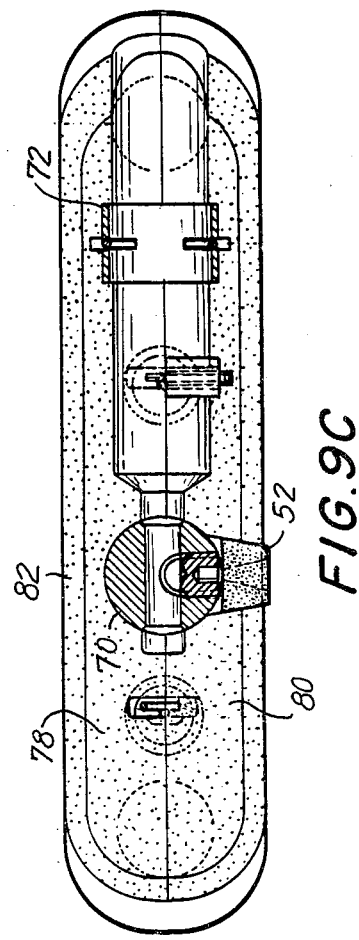

PACER ELECTRODE CONNECTOR ASSEMBLY

DESCRIPTION

This invention relates to connector assemblies for heart pacers, and more particularly to such assemblies for use with two bipolar electrode lead proximal terminations.

Most implantable heart pacers in current use have only one or two active stimulating terminals. Typically, those units with two terminals are either single-channel bipolar types, or dual unipolar types. In the case of a dual unipolar type, the stimulating terminal of each channel is electrically insulated from the metal case of the device, and the case is used as the indifferent electrode for both active circuits.

Less commonly used are heart pacers with three or four electrically insulated terminals, with the metal case serving as a fourth or fifth electrode. One major reason for this is the volume and geometry of the connector assembly required to connect four conventional unipolar electrode leads to the pulse generator.

Dual chamber heart pacers are being used more and more frequently. Especially if such a pacer is to allow for stimulation or sensing of each chamber over a unique pair of leads, it is apparent that the connector assembly must allow for more than two electrode lead connections. Although the subject invention has application to unipolar leads, its main advantage is with use of bipolar leads, allowing up to four electrode terminations to be made. This is especially true where each bipolar electrode lead has a proximal termination, which is placed in a respective insertion bore of the connector assembly, in the form of a forward pin contact and a rearward annular ring contact. In such a case, the connector assembly consists of a plastic housing with two insertion bores, the housing being secured to the pulse generator case. Embedded within the plastic housing are four metallic termination blocks, one pair of termination blocks being allocated to the two contacts on each electrode lead proximal termination. Electrical contact is made within the plastic housing between each terminal block and one of the lead-through terminals which extend out of the pulse generator case.

Our invention relates to the manner in which the connector assembly is made. The closest prior art, to be described in detail below, involves the molding of the connector assembly plastic housing around metallic termination blocks held within the mold. A mechanism is provided for securing the plastic housing to the pacer case and for connecting the lead-through terminals to respective termination blocks within the connector assembly. However, there are several problems with even this prior art method of pacer construction.

It is a general object of our invention to provide a pacer with an improved connector assembly and an improved method of making it.

Briefly, in accordance with the principles of our invention and in the illustrative embodiments thereof, two in-line pairs of metallic termination blocks are connected by four wires to respective lead-through terminals. At least two fluid-insulating metal-free plastic parts (molded without embedding termination blocks in them) are then slid on the assembly to insulate the termination blocks and to provide a pair of insertion bores for the two electrode lead proximal terminations. The plastic parts are shaped to lock onto capped studs provided on the case, and the plastic parts are sealed to each other.

In one embodiment of the invention, conventional grub screw termination blocks are used for both the forward pin contacts and the rearward annular ring contacts. In a second embodiment of the invention, however, a different kind of termination block is used for the annular ring contacts. Each of these termination blocks consists of a simple hollow cylinder having a plurality (preferably, three) of equally spaced circumferential cuts. A contact wire is wrapped around the cylinder, sits in the cuts, and extends into the cylinder bore. The wire segments which sit in the cuts grip the circumference of the annular ring contact when the proximal termination is inserted. An added advantage of this construction is that the same wire which engages the annular ring cntact may be connected directly at its other end to a lead-through terminal, thus avoiding an additional welding step which would otherwise be necessary.

Further objects, features and advantages of the invention will become apparent upon consideration of the following detailed description in conjunction with the drawing, in which:

FIG. 6 is a perspective view of the first embodiment of the invention, showing the manner in which the several individual parts are fitted together (it being understood that element 44, while depicting only the top of the pacer case, represents the entire pulse generator);

FIG. 8 is a perspective view of the second embodiment of the invention, showing the manner in which the several individual parts are fitted together; and FIG. 9A is a sectional view through the assembled connector assembly of FIG. 6, and FIGS. 9B-9E are sectional views through respective lines 9B—9B through 9E—9E of FIG. 9A;

Figure 1:
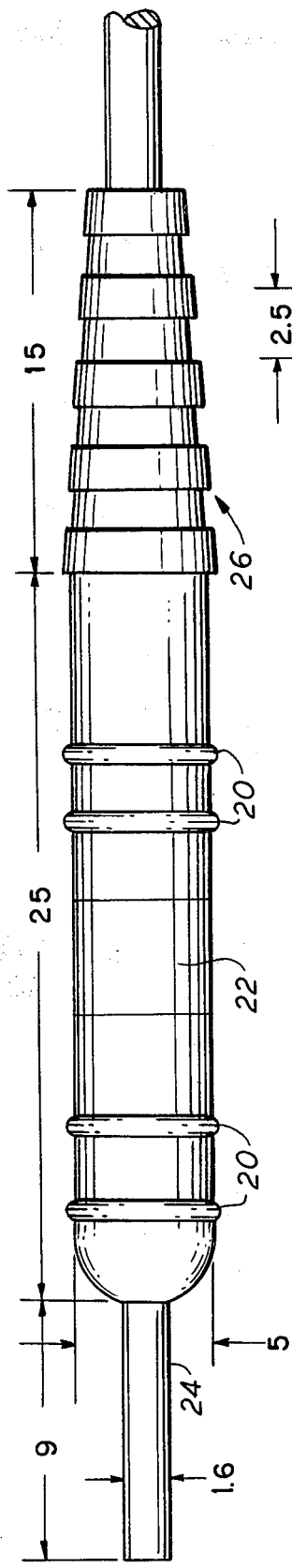
FIG. 1 depicts a conventional type bipolar electrode lead proximal termination with a unipolar proximal termination profile.

The difficulty in providing a connector for four conventional unipolar leads can be appreciated by considering FIGS. 1-3, 4A and 4B. FIG. 1 depicts the proximal termination of a conventional type heart pacer electrode lead. Actual dimensions are illustrated in order that the necessary connector volume and geometry, as depicted in the other figures, be appreciated. The overall diameter of the proximal termination is 5 mm, excluding the additional width of the sealing rings 20. The proximal termination of FIG. 1 includes a conductive ring 22, if the lead is bipolar. A bipolar lead is one which includes two conductors which extend to the distal end, the two conductors typically being in the form of superimposed helixes which are insulated from each other. One helix terminates in the rearward annular ring 22, and the other terminates in the forward metal tip or pin 24. In the absence of any connection in the connector assembly to ring 22, the lead can function in a unipolar fashion; the annular ring is electrically sealed off from tip 24 in the bore of the connector assembly by a first pair of sealing rings, and by a second pair of sealing rings from body fluids. If, on the other hand, the lead is to function in a bipolar fashion, two connections are made in the connector assembly, one to the tip 24 and the other to the annular ring 22. Leads of this type are conventional and are illustrated, for example, in prior art U.S. Pat. Nos. 4,236,525 and 4,301,805. The illustrative embodiments of the invention utilize bipolar leads, and it for this reason that such a lead is shown in FIG. 1. However, the geometry problems which almost necessitate the use of bipolar leads can be appreciated by considering the dimensions of unipolar proximal terminations and the connector assembly configurations which are required to accommodate them. The dimensions of unipolar proximal terminations are basically the same as those of bipolar proximal terminations, and thus the dimensions of FIG. 1 are equally applicable to unipolar leads.

As illustrated in FIG. 1, the overall length of the proximal termination of the electrode lead is 40 mm, with a 9-mm metal tip 24. The diameter of the tip or pin is typically 1.6 mm. The most common technique for connecting the electrode lead proximal termination of FIG. 1 to a heart pacer is to make use of a grub screw. The grub screw has the advantage of providing both a reliable electrical connection and a strong mechanical connection which can be relied upon to resist withdrawal forces applied to the lead during implant. However, the grub screw must be made of high tensile strength metal in order to achieve reliable performance; this, in turn, requires that it be insulated from contact with body fluids. A typical length of a grub screw is 2 mm, and at least 2 mm of insulation is usually used to insulate the screw from body fluids.

Figure 2:
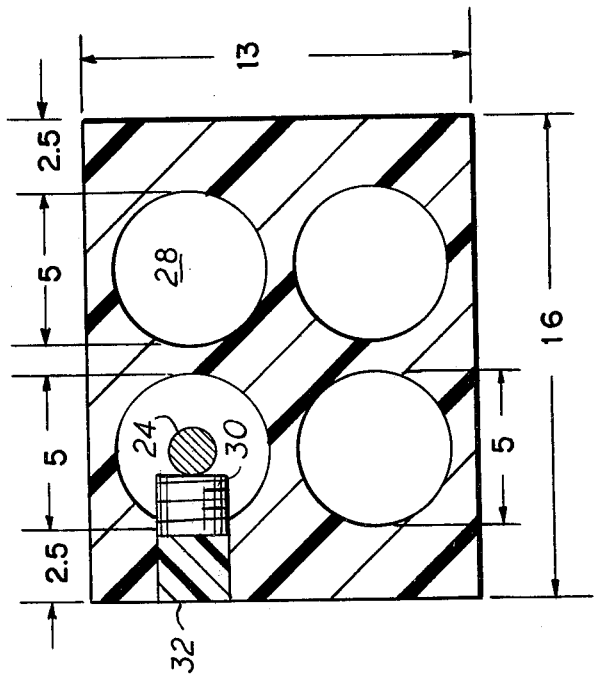

Given the minimum insulation requirements and the typical size of an electrode lead proximal termination, FIG. 2 depicts the dimensions of a connector assembly required to house four electrode lead proximal terminations. The exact manner of establishing a connection to each of the four pins 24 (only one of which is shown in FIG. 2) is not illustrated; all that is shown are four 5-mm bores 28, in one of which a pin 24 is illustrated. A grub screw 30 is shown screwed into the bore and making contact with pin 24; the manner in which the electrical connection is made to a pacer lead-through terminal or the pin itself is not depicted. Plastic plug 32 has a length of 2 mm, and it is assumed that the corresponding grub screw and plastic plug for each of the other bores extends to the left or the right in the drawing. It is also assumed that there is at least a 1-mm thickness of insulating connector assembly material surrounding each electrode lead proximal termination. This is the minimum thickness required for plastic materials to maintain structural integrity in an implant situation. Based on the dimensions shown in FIG. 2, it is apparent that the connector assembly used to house the four proximal terminations must be in the order of $13 \times 16$ mm. The pacer case would sit below the assembly of FIG. 2, and it is apparent that the overall width of the assembly would be about 6 mm greater than the acceptable 10 mm thickness of a state-of-the-art heart pacer.

Figure 3:
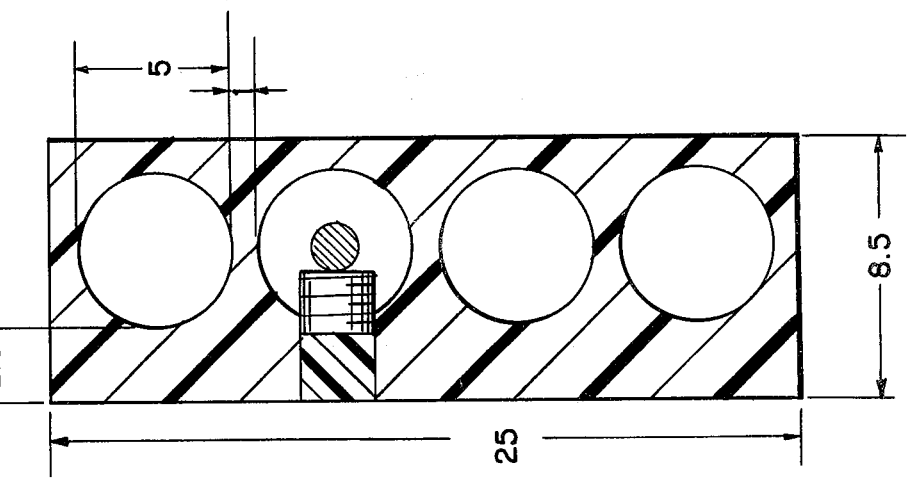
FIGS. 2 and 3 illustrate two different connector assembly geometries which will be helpful in understanding the difficulty in using four unipolar electrode lead proximal terminations if four electrode connections are required.

FIG. 3 depicts an alternative arrangement in which the four electrode lead proximal terminations are in line with each other, with a 1-mm thickness of insulating connector material once again surrounding each termination. Although the thickness of the connector in this case need be only 8.5 mm, the length is 25 mm, a length which is much larger than any commercially acceptable product on the market.

Figure 4B:
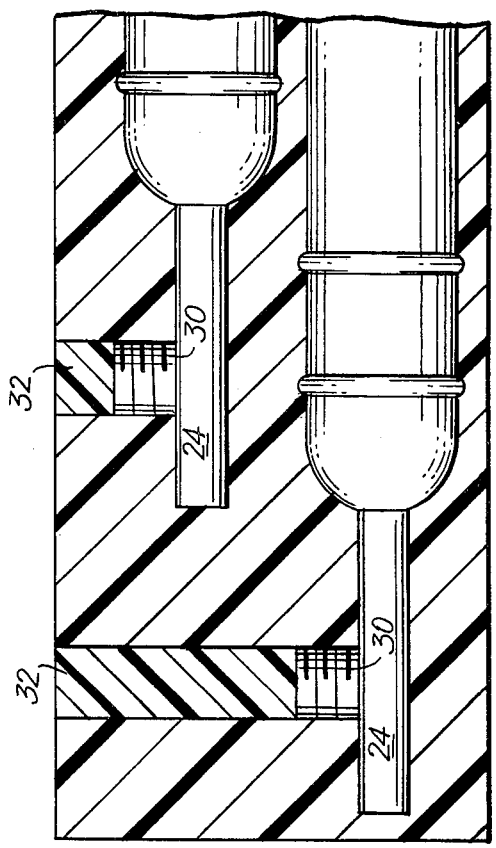
FIGS. 4A and 4B are front and side illustrations of still another connector assembly configuration, and will be helpful in explaining how even offsetting the proximal terminations still does not make it practical to use four unipolar proximal terminations.

The arrangements of both FIGS. 2 and 3 involve what is known as "side entry". With the pacer case being at the bottom of each of the connector assemblies of FIGS. 2 and 3, the grub screws are inserted from one or both sides of the connector assembly. The arrangement of FIGS. 4A and 4B, with FIG. 4B representing a side view of the connector assembly of FIG. 4A, involves what is known as "top entry", with the electrode lead proximal terminations being offset along their lengths. (Once again, the manner in which electrical connections are actually established to the pacer case are not depicted.) It should be noted that with respect to each pair of terminations, one of which is on top of the other, the pins 24 are offset from each other. This means that one grub screw has to be screwed further down in the connector assembly than the other, requiring a correspondingly longer plastic plug 32. If a 1-mm thickness of insulating connector body material is once again provided around each termination, it is apparent that the overall dimensions of the connector block are reduced from $13 \times 16$ mm as in FIG. 2, to $13 \times 14.5$ mm. However, a thickness of 13 mm is too large for practical use.

It is considerations such as these which lead to the conclusion that bipolar leads of the type depicted in FIG. 1 are necessary. This allows four separately insulated electrode conductors to be connected in the volume normally required for only two unipolar electrode lead proximal terminations. The use of two such bipolar leads offers the following advantages:

(1) The arrangement preserves the advantages of the large-diameter electrode lead proximal termination, namely, a diameter large enough to permit a gradual stress-relieving taper, shown by the numeral 26 in FIG. 1, so as to reduce the stress which would otherwise occur were a smaller diameter termination to exit abruptly from a rigid connector. It is also well suited to electrically terminating helices which in the main body of the lead would be disposed coaxially around each other. The coaxial geometry is advantageous because it minimizes lead diameter while featuring improved fatigue strength as opposed to that exhibited by side-by-side helices.

(2) Because of the provision of sealing rings 20 in FIG. 1, on both the proximal and distal sides of metal ring 22, the termination is suitable for use not only as a bipolar termination, but also as a unipolar termination as described above; the ring 22 is electrically insulated by the sealing rings from both the tip 24 and body fluids.

(3) Standard unipolar electrode lead proximal terminations without rings such as ring 22 in FIG. 1 can be used in pacers designed to accept ringed terminations without the need for any adaptors (assuming that the pacer case, for example, is used as an electrode) because the dimensions of a ringed termination are the same as those of an existing unipolar termination.

(4) The use of two ringed terminations permits almost any mode of pacing therapy to be used. Up to two conductors may be present in each heart chamber giving the choice, in conjunction with the metal pacer case, of several different modes of operation, assuming that the associated pulse generator is provided with a mechanism for switching its output terminals among the choice of electrodes available to it.

The use of two ringed terminations of the type shown in FIG. 1 provides a 5-terminal pacer (the metal case being considered to be a terminal). The pacer would be extremely flexible in application, thereby reducing the probability of the need for surgical reintervention following the initial implant. All of these advantages will accrue only if multiple connections can be made in a connector of acceptable size and thickness. Fortunately, connector size and thickness present no problems since if only two terminations are to be inserted into the connector, instead of four as in conventional 4-terminal devices, a connector design of the order of 10-mm thickness is easily achievable by stacking one termination on top of the other. (Were the terminations to be placed side-by-side, the thickness of the connector would still be greater than 10 mm, the more or less industry design standard.) Pulse generator thickness is the most significant factor when it comes to patient comfort, especially for those patients with less than normal fatty tissue. Thus it is apparent that the optimum connector would be one which accommodates a pair of vertically stacked ringed electrode lead proximal terminations.

However, connector manufacturing techniques are equally important design considerations. There are generally three different types of prior art connector manufacturing techniques:

(1) The most common method of constructing a connector body has been by casting epoxy resin or similar thermosetting polymer material in situ over the preassembled metallic components. Casting in situ permits the use of miniature lead-throughs which do not directly support the metal termination blocks, and it also allows the lead-throughs to be made of materials otherwise unsuited to direct exposure to body fluids. The metal termination blocks are supported directly by the cured resin which also surrounds and insulates all of the components. What is commonly done is to key the resin into raised metal projections welded to the case so that no direct stresses are applied to the fragile miniature lead-throughs during handling at implant. However, in situ casting offers serious limitations. Imperfections in the casting may cause the entire device to be rejected on cosmetic grounds leading to increased manufacturing costs. The casting material may fail to insulate electrically due to the lack of surface bonding to some components. The shrinkage of the thermosetting resins may damage the fragile glass or ceramic lead-throughs as a result of stresses generated during the curing cycle. Finally, the process is unsuited to casting around any components which might be required to flex or move in service, since it is very difficult to prevent the uncured resin from flowing in and around such components and thus rigidizing them.

(2) The second technique in current use entails the use of strong self-supporting combined terminal/lead-throughs, insulated by a flexible elastomer molding. This technique offers the advantage of allowing different diameter lead terminations to be utilized without the need of any adaptors, while at the same time providing an easily mountable/demountable connector of predictable high quality. However, this technique is not possible for use with ringed terminations of the type depicted in FIG. 1 because the combined terminal/lead-throughs must be of large diameter since they are self-supporting. It is not possible to make a connection of the ring of the upper termination without having a large rigid support passing along the side of the lower termination, thus greatly adding to the thickness of the connector itself. While the technique is well suited to side-by-side lead arrangements, a side-by-side arrangement in and of itself gives rise to unacceptable thickness.

(3) The third technique is common use is exemplified by U.S. Pat. Nos. 4,142,532, 4,182,345 and 4,226,244. This technique involves precasting metal termination blocks in a molded thermoplastic body. The thermoplastic body is held onto the generator case by posts containing tapered keys, by screws, or by other means. The connector is thus easily mountable/demountable, and it can have a predictable high quality.

Figure 5B:
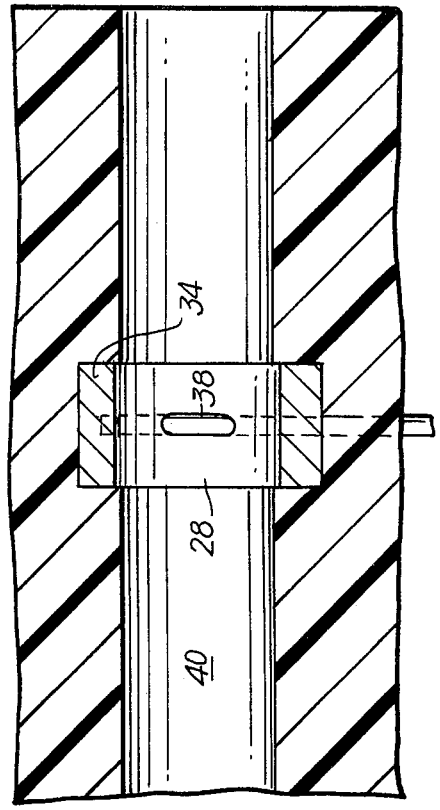
FIGS. 5A and 5B illustrate front and side views of a general prior art technique for establishing a connection to the annular ring contact of a bipolar proximal termination.
Figure 4A:
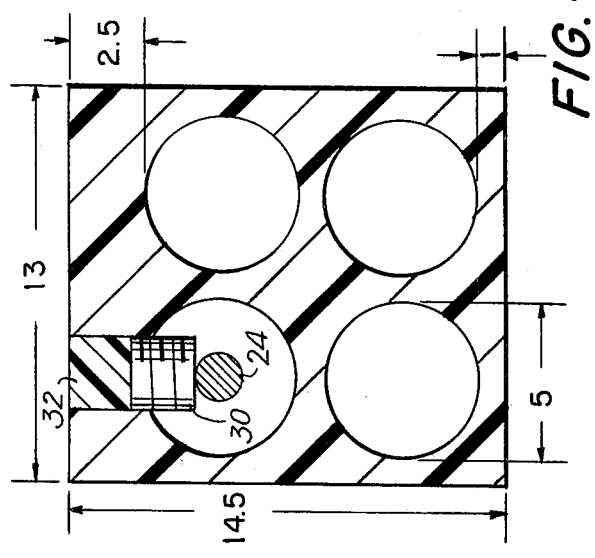
Figure 5A:
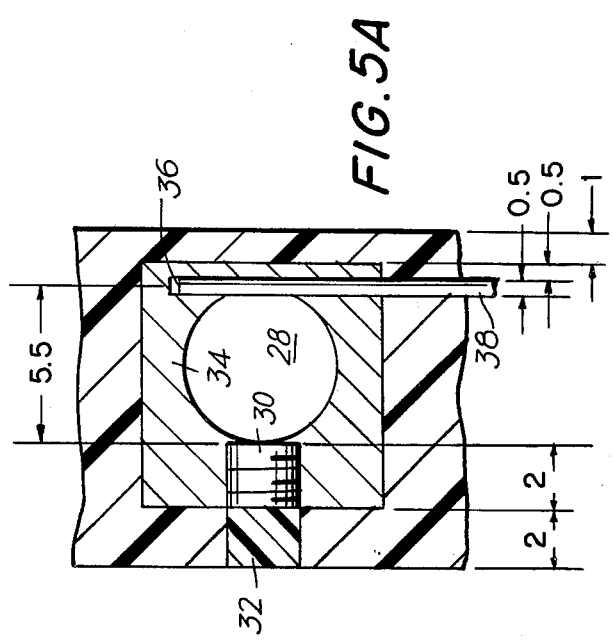

When using the third technique, there must be some way to electrically connect each termination block within the plastic connector body to a lead-through terminal which exits the pacer case. The technique exemplified by the three above-identified patents is depicted in FIGS. 5A and 5B as applied to establishing a connection to annular ring 22 of FIG. 1. Metal termination block 34 is contained within the molded plastic connector body. In addition to a bore 28 for insertion of the electrode lead proximal termination, there is an additional vertical bore 36. This bore accepts a lead-through wire 38 which passes directly from the lead-through in the pacer case. As grub screw 30 is screwed into metal block 34, it bears against annular ring 22 and forces the ring against wire 38. It is in this manner that the grub screw controls not only a mechanical securement of the proximal termination, but also electrical contact from annular ring 22 to wire 38. A similar termination block may be used for pin 24 of the proximal termination, although bore 28 would be smaller in such a case thus allowing smaller dimensions for the termination block. The two termination blocks would be in line with each other, with another pair of termination blocks being placed above the first pair for establishing connections to the second proximal termination.

But while the technique is advantageous for establishing a connection to a pin 24, it is not adequate for establishing a connection to an annular ring 22. That is because in the latter case the bore 28 must accommodate a 5-mm annular ring as opposed to a 1.6-mm pin. This gives rise to an overall thickness of 11 mm in FIG. 5A, even assuming that minimum length components are used (a 2-mm insulator 32 and a 2-mm grub screw 30), and allowing for sufficient metal on the right side of wire 38 to support it against deformation and 1-mm insulation on the right side of the connector body. This exceeds the more or less standard 10-mm thickness which is state-of-the-art.

It should be noted that it is not possible to avoid use of the metal termination block in order to reduce the connector body thickness and to use a plastic grub screw which would bear directly against ring 22 and force it against wire 38. Plastic grub screws are subject to creep and this completely destroys the reliability of the high-pressure contact which is the main advantage of the metal grub screw connection. Eliminating the metal termination block has the same effect.

Another problem with extending the prior art technique for use with a bipolar lead is that four lead-through wires 38 must be correctly oriented simultaneously when the connector body is mounted on the pacer case. While this is relatively easy for two lead-through devices, it is more difficult in the case of a four lead-through unit.

Still another problem with the application of the prior art technique for establishing a connection to annular ring 22 can be appreciated by reference to FIG. 5B. Bore 40 in the connector body itself must have a diameter of 5 mm in order to rigidly seat the proximal termination whose outer diameter is 5 mm. But bore 28 in the metal termination block must be slightly larger in diameter because it must expose approximately half of the diameter of the lead-through wire 38. This means that the diameter of bore 28 must be 5.5 mm (for a 1-mm thick wire 38), and bore 28 is shown in FIG. 5B as being slightly larger than bore 40. In molding the connector body around the metal termination block, the block is aligned by pins extending into bore 28. But this means that in the molding process itself bore 40 is formed around the pins and must necessarily have a diameter of 5.5 mm. This, in turn, means that bore 40 as originally molded is slightly oversized, and must be reduced after the molding step by the placement of tube inserts. It must be recalled, however, that sealing rings 20 on the proximal termination of FIG. 1 must make very tight contact with the walls of the bore which contains them in order to electrically isolate annular ring 22. This becomes difficult to achieve if tube inserts are used. Thus one of the main problems with using the prior art technique to establish a connection to an annular ring 22 is that the connector body and the metal termination block must have slightly different bore sizes.

In accordance with a key feature of our invention, a plastic connector body is not molded around metal termination blocks. Instead, the plastic connector body is molded separately (although not necessarily as a single integral element). The metal termination blocks are attached to the lead-throughs and only then are the plastic parts of the connector body put into place. The four termination blocks are assembled onto the pulse generator case and are supported in space on their respective connecting wires. The plastic connector body parts are then slid over and onto the preassembled components, with all voids being filled or coated with standard medical-grade sealant/adhesive. Two embodiments of the invention are illustrated, the first in FIGS. 6 and 7A-7E. The pacer electrode connector assembly can be best appreciated by referring to the exploded perspective view of FIG. 6, although FIGS. 7A-7E will be helpful in understanding some of the relationships between the parts.

Conventional grub screw connections are used for establishing the four electrical connections. The top of the pacer case 44 is shown with four conventional lead-throughs 58, each lead-through having an upstanding central terminal which is connected internally to the pacer circuitry (not shown). Four wires 60 are provided, one end of each wire being welded or soldered to the terminal of a respective lead-through and the other end being soldered to a termination block 46 or 48. Each termination block is provided with a conventional grub screw 62, and a central bore 46a or 48a. Each of bores 46a is larger in diameter than the in-line bore 48a in order to accommodate annular ring 22 (FIG. 1), with the smaller bore 48a accommodating pin 24 (FIG. 1). In each case, the grub screw mechanically secures the ring or the pin to the respective termination block, and an electrical connection is established to the respective lead-through terminal. It should be noted that the two pairs of termination blocks are offset relative to each other in the direction of proximal termination insertion.

The case 44 also includes two capped studs 44a for securing thermoplastic molding 50 in place.

The thermoplastic molding 50 is an integral element which is slid in the direction shown onto case 44. Element 50 is molded so that it fits over all of the preassembled components on case 44. The molding includes two cut-outs 50a which slide over the caps of the two studs 44a. This restricts movement of molding 50 to only one direction, namely, a direction opposite to that in which the molding is initially slid in order to place it on the case. Even this movement is prevented, however, by filling the void at the open end of each of cut-outs 50a with sealant/adhesive.

After molding 50 is secured in place, insert 56 is slid into a cut-out 50b in molding 50 in the direction shown, and sealed in place with sealant/adhesive. The purpose of the insert (which includes a central bore to accommodate the upper proximal termination) is to fill the void of cut-out 50b. The cut-out is necessary in the first place in order that molding 50 be able to slide onto the case without interference from wire 60 which connects the upper termination block 46a to its respective lead-through terminal. Thereafter, cap 54 is placed over the entire assembly to provide positive fixation and insulation. A series of injection holes 54a on the cap are used for the injection of sealant/adhesive to fill all remaining voids. The cap is held in place by the use of sealant/adhesive, although this can be augmented by cross pins if desired. The injection holes are placed in cap 54 so that sealant/adhesive may be injected at precise locations in order that it flow into each void.

Silicone elastomer sealing plugs 52 are then compressed and placed into holes 50c in molding 50 and into holes 54b of cap 54 in order to seal off the grub screws 62 from contact with body fluids. The sealing plugs are also fixed in place with sealant/adhesive.

Movement of plastic part 50 is prevented because it is interlocked on the studs 44a, with the open ends of voids 50a being sealed with sealant/adhesive and cap 54 being similarly sealed in place. It is also possible to fill the cavity which remains at the open end of each cutout 50a adjacent to each stud 44a with an additional thermoplastic element, in which case less sealant/adhesive would have to be injected through cap 54 in order to fill the voids.

Any forces which are developed on cap 54 are developed in directions which are perpendicular to the direction in which the cap is initially slid into place. This means that there are no effective forces acting to detach the cap. The sealant/adhesive which is used, together with the sealing plugs 52 which pass through holes in both the cap and the molding 50, are sufficient to retain the cap in place on the molding.

It should be noted that cap 54 includes two holes 54c. These holes align with bores 50d in molding 50, which in turn align with the bores in the termination blocks, thus giving rise to insertion bores for two proximal terminations.

Figure 7B:
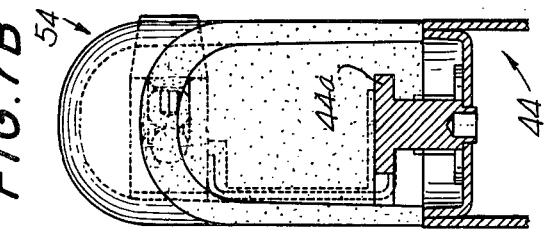
FIG. 7A is a sectional view through the assembled connector assembly of FIG. 6, and FIGS. 7B-7E are sectional views through respective lines 7B—7B through 7E—7E of FIG. 7A.
Figure 7E:
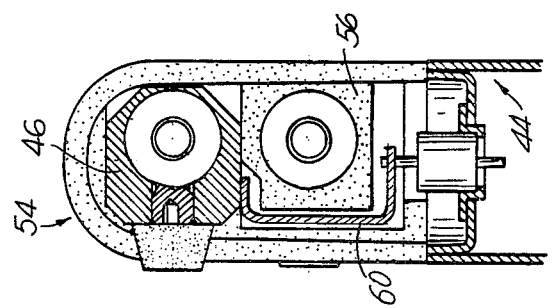
Figure 7D:
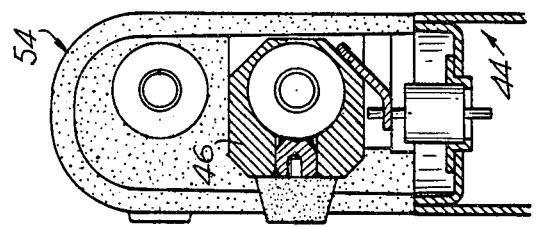
Figure 7A:
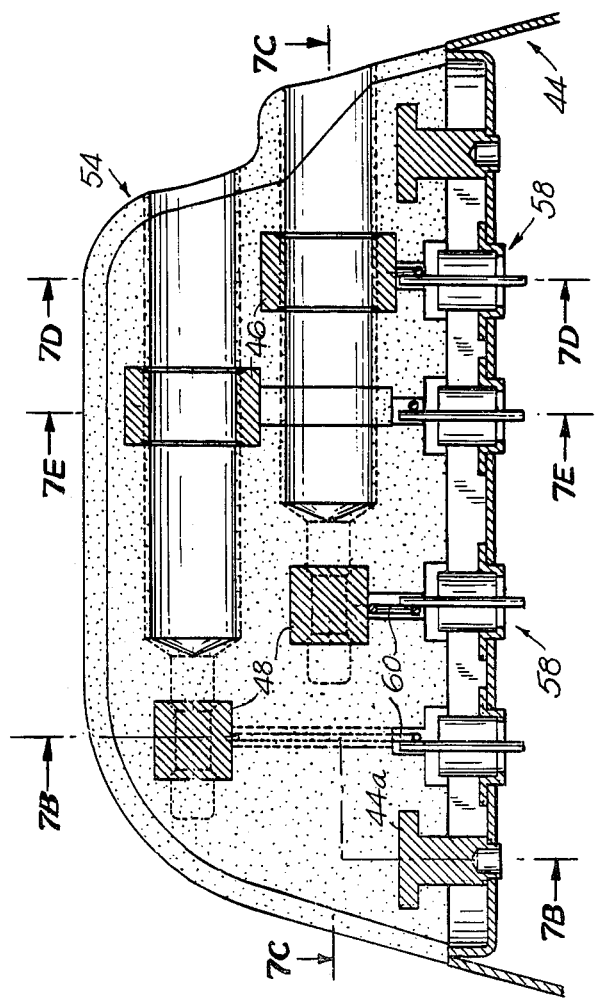
Figure 7C:
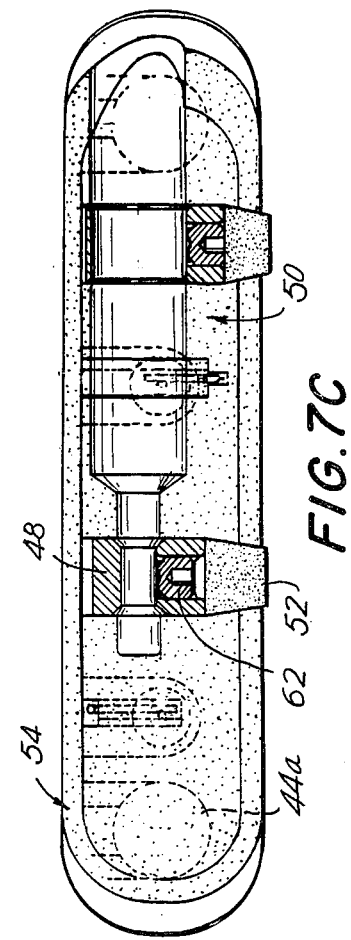

The embodiment of the invention shown in FIGS. 6-7E provides all of the advantages of the prior art without, however, requiring the molding of a plastic connector body around metal termination blocks. It also facilitates manufacture; for example, there is no need to insert a connector body in place while trying to ensure that four wires simultaneously slide into vertical bores in termination blocks (see FIG. 5A). It is also apparent that the construction allows a minimum thickness to be achieved.

The second embodiment of the invention is shown in perspective view in FIG. 8, and in sectional views in FIGS. 9A-9E. The major difference between the two embodiments of the invention is that in the second grub screws are not required for making connections to the annular rings 22 (FIG. 1).

The top of the case 44 in FIG. 8 is similar to that in FIG. 6. Termination blocks 70 in FIG. 8 are secured to the lead-throughs by wires 60, as are termination blocks 48 in FIG. 6, although the termination blocks in FIG. 8 have a different shape. Standard grub screws 62 are used to secure a pin of each proximal termination to one of the termination blocks. But instead of using an additional pair of similar termination blocks 46 as in FIG. 6, the connector assembly of FIG. 8 employs two cylindrical metal tubes 72, each of which incorporates three saw cuts 72a symmetrically disposed around the tube. Seated in the three cuts of each cylindrical metal tube termination block is a wire 74 which is connected to the terminal which extends up through a respective lead-through. Wires 74 should be pre-tensioned and made of titanium, titanium alloy, stainless steel, or other implant-quality, high tensile strength material.

The annular ring on the proximal termination which is inserted in either of the two cylindrical metal tubes 72 makes contact with the three straight wire segments contained in the cuts. Three-point contact is preferred because it tends to centralize the proximal termination in the block. The three wire segments are at 120-degree spacings around the tube (see FIGS. 9D and 9E), and they arc slightly to conform to the diameter of the annular ring. The wire is constrained to remain within the cylindrical tube into which the proximal termination is inserted due to the wire being constrained within the three cuts. The compressive forces exerted by the wire 74 on the proximal termination may be controlled by varying the length of each cut, the diameter of tube 72, and the diameter of the wire. Preferably, the lengths of the cuts are chosen so that each straight segment of the wire just fails to penetrate into the tube bore beyond the inner wall surface of the tube, as seen most clearly in FIGS. 9D and 9E, in order to discourage distortion of the wire upon insertion and removal of the proximal termination.

Instead of utilizing a single molding 50 as in FIG. 6, two moldings 78, 80 are utilized. The two moldings are almost mirror images of each other, although molding 78 includes an additional cut-out so that the descending wire 74 of the upper tube 72 can be contained. An additional molded element 76 is inserted in this cut-out in order to seal the cavity which contains the wire. Each molded part includes cut-outs 78a, 80a for mating with capped studs 44a to achieve the same result as in the connector assembly of FIG. 6. Cover cap 82 is comparable to cover cap 54 in FIG. 6 and serves to interlock the molded parts 78, 80 in place, and to lock them onto studs 44a.

The two molded parts 78, 80 include cavities 78c, 80c; the diameter of each cavity is chosen to be approximately 0.1 mm larger than the diameter of the respective wire 74 which it contains so that high contact pressure is maintained on all three wire segments in each tube 72. This causes each wire segment to bend into an arc when the proximal termination is inserted, rather than to cause an unequal unwrapping of the wire triangle which would otherwise occur in the absence of this constraint.

Although injection holes are not shown in cover 82 in FIG. 8, it is to be understood that injection holes comparable to holes 54a of FIG. 6 are provided, in order that sealant/adhesive may be injected at precise locations and flow into each void as necessary to fill it. All contact surfaces are coated with sealant/adhesive at assembly. Because there are only two grub screws in the assembly of FIGS. 8-9E, only two sealing plugs 52 are required. These plugs are inserted through holes 82a in the cover cap and holes 78b in one of the two central moldings.

One advantage of the second embodiment of the invention is that the surgeon has only two grub screw connections to make, as opposed to four such connections in the first embodiment of the invention. While the implant task is thus simplified, the connections established in the second embodiment of the invention are just as reliable as those established in the first. An added advantage of the arrangement of FIGS. 8-9E is that there is no possibility of damage to an annular ring on the proximation terminal due to an excessive grub screw compression force.

It will be noted that in the arrangement of FIG. 6, each end of each of wires 60 must be soldered or welded, either to a lead-through terminal or to a termination block. Still another advantage of the arrangement of FIG. 8 is that each of the wires used to establish contact with an annular ring need be welded at only one end—that end connected to the lead-through terminal. The wire welded to the lead-through terminal makes direct contact with the annular ring on the proximal termination, and there is no need to weld it to a termination block or to a metal tube 72. In fact, the lead-through wire itself can be used to make the direct connection without the need for any weld if it is made long enough and it is of sufficient tensile strength. It is to be noted, however, that strength is often lost in lead-through wires when they are heated during lead-through manufacture.

Although it is less favored, it is also possible to provide tube 72 with internal spring contacts for bearing against the annular rings of proximal terminations. However, this would require not only contact from spring to tube, but also the provision of an additional wire connection from the tube to the lead-through terminal. It is to be understood that the more joints in the system, the less the inherent reliability.

The system of FIGS. 8-9E offers all of the advantages of the system of FIGS. 6-7E. Although two molded parts 78, 80 are used instead of only one molded part 50, this in and of itself offers no major advantage and is intended simply to illustrate an alternative construction. The major advantage of the second embodiment of the invention over the first is that the conventional grub screw connections are avoided, with the same wire which is connected to the lead-through terminal also serving to establish the connection to the annular ring of the electrode lead proximal termination.

Although the invention has been described with reference to particular embodiments, it is to be understood that these embodiments are merely illustrative of the application of the principles of the invention. Numerous modifications may be made therein and other arrange-

We claim:

1. A connector assembly for connecting two bipolar electrode lead proximal terminations to four terminals extending through the case of a heart pacer; each of said bipolar electrode lead proximal terminations having a forward pin and a rearward annular ring; comprising four metallic termination blocks each for electrical connection to a respective one of said terminals; and at least two secured fluid-insulating metal-free plastic parts which make slidable engagement with each other and at least one of which makes slidable engagement with said four metallic termination blocks and said case; pairs of said metallic termination blocks having aligned bores therein and said at least two secured plastic parts forming respectively aligned bores to accommodate the insertion of two bipolar electrode lead proximal terminations.

2. A connector assembly in accordance with claim 1 wherein a first pair of said metallic termination blocks is disposed above a second pair of said metallic termination blocks relative to said case, and the blocks in one pair are offset from the blocks in the other pair in the direction of bipolar electrode lead proximal termination insertion.

3. A connector assembly in accordance with claim 2 wherein said case includes a pair of upstanding capped studs, and at least one of said plastic parts includes a pair of cut-outs for making locking sliding engagement with respective ones of said capped studs.

4. A connector assembly in accordance with claim 3 wherein each of said metallic termination blocks includes screw securing means.

5. A connector assembly in accordance with claim 4 wherein a first of said plastic parts make slidable engagement with said four metallic termination blocks and said case from the side of said case, and a second of said plastic parts is a cap which makes slidable engagement with said first of said plastic parts from above said case.

6. A connector assembly in accordance with claim 3 wherein each of at least two of said metallic termination blocks includes a hollow cylinder having a plurality of circumferential cuts therein, and a wire in electrical contact at one end with a respective terminal and having its other end wrapped around said cylinder and sitting in said cuts, with said wire extending through said cuts past the inner wall of said hollow cylinder.

7. A connector assembly in accordance with claim 6 wherein said hollow cylinder has three circumferential cuts therein.

8. A connector assembly in accordance with claim 6 wherein the outer surface of said wire does not extend through said cuts past the inner wall of said hollow cylinder.

9. A connector assembly in accordance with claim 6 wherein the entire length of any wire segment which is contained in any of said cuts is straight in the absence of the insertion of a respective electrode lead proximal termination.

10. A connector assembly in accordance with claim 9 wherein at least two of said plastic parts surround the wire wrapped around said cylinder to force all wire segments contained in said cuts to bend in arcs upon the insertion of an electrode lead proximal termination.

11. A connector assembly in accordance with claim 6 wherein first and second ones of said plastic parts make slidable engagements with said four metallic termination blocks and said case from the sides of said case, and a third of said plastic parts is a cap which makes slidable engagement with said first and second plastic parts from above said case.

12. A connector assembly in accordance with claim 1 wherein said case includes a pair of upstanding capped studs, and at least one of said plastic parts includes a pair of cut-outs for making locking sliding engagement with respective ones of said capped studs.

13. A connector assembly in accordance with claim 1 wherein each of said metallic termination blocks includes screw securing means.

14. A connector assembly in accordance with claim 13 wherein a first of said plastic parts makes slidable engagement with said four metallic termination blocks and said case from the side of said case, and a second of said plastic parts is a cap which makes slidable engagement with said first of said plastic parts from above said case.

15. A connector assembly in accordance with claim 1 wherein each of at least two of said metallic termination blocks includes a hollow cylinder having a plurality of circumferential cuts therein, and a wire in electrical contact at one end with a respective terminal and having its other end wrapped around said cylinder and sitting in said cuts, with said wire extending through said cuts past the inner wall of said hollow cylinder.

16. A connector assembly in accordance with claim 15 wherein said hollow cylinder has three circumferential cuts therein.

17. A connector assembly in accordance with claim 15 wherein the outer surface of said wire does not extend through said cuts past the inner wall of said hollow cylinder.

18. A connector assembly in accordance with claim 15 wherein the entire length of any wire segment which is contained in any of said cuts is straight in the absence of the insertion of a respective electrode lead proximal termination.

19. A connector assembly in accordance with claim 18 wherein at least two of said plastic parts surround the wire wrapped around said cylinder to force all wire segments contained in said cuts to bend in arcs upon the insertion of an electrode lead proximal termination.

20. A connector assembly in accordance with claim 15 wherein first and second ones of said plastic parts make slidable engagements with said four metallic termination blocks and said case from the sides of said case, and a third of said plastic parts is a cap which makes slidable engagement with said first and second plastic parts from above said case.

21. A connector assembly in accordance with claim 1 wherein a first of said plastic parts makes slidable engagement with said four metallic termination blocks and said case from the side of said case, and a second of said plastic parts is a cap which makes slidable engagement with said first of said plastic parts from above said case.

22. A connector assembly in accordance with claim 1 wherein first and second ones of said plastic parts make slidable engagements with said four metallic termination blocks and said case from the sides of said case, and a third of said plastic parts is a cap which makes slidable engagement with said first and second plastic parts from above said case.

23. A heart pacer comprising a pulse generator; a case containing said pulse generator with two terminals extending from said pulse generator through said case; and a connector assembly for connecting a bipolar electrode lead proximal termination to said two terminals; said bipolar electrode lead proximal termination having a forward pin and a rearward annular ring; said connector assembly including two metallic termination blocks each electrically connected to a respective one of said terminals; and at least two secured fluid-insulating metal-free plastic parts which make slidable engagement with each other and at least one of which makes slidable engagement with said two metallic termination blocks and said case; said metallic termination blocks having aligned bores therein and said at lest two secured plastic parts forming an aligned bore to accommodate the insertion of a bipolar electrode lead proximal termination.

24. A heart pacer in accordance with claim 23 wherein said case includes a pair of upstanding capped studs, and at least one of said plastic parts includes a pair of cut-outs for making locking sliding engagement with respective ones of said capped studs.

25. A heart pacer in accordance with claim 23 wherein each of said metallic termination blocks includes screw securing means.

26. A heart pacer in accordance with claim 25 wherein a first of said plastic parts makes slidable engagement with said two metallic termination blocks and said case from the side of said case, and a second of said plastic parts is a cap which makes slidable engagement with said first of said plastic parts from above said case.

27. A heart pacer in accordance with claim 23 wherein one of said two metallic termination blocks includes a hollow cylinder having a plurality of circumferential cuts therein, and a wire in electrical contact at one end with a respective terminal and having its other end wrapped around said cylinder and sitting in said cuts, with said wire extending through said cuts past the inner wall of said hollow cylinder.

28. A heart pacer in accordance with claim 27 wherein said hollow cylinder has three circumferential cuts therein.

29. A heart pacer in accordance with claim 27 wherein the outer surface of said wire does not extend through said cuts past the inner wall of said hollow cylinder.

30. A heart pacer in accordance with claim 27 wherein the entire length of any wire segment which is contained in any of said cuts is straight in the absence of the insertion of an electrode lead proximal termination.

31. A heart pacer in accordance with claim 30 wherein at least two of said plastic parts surround the wire wrapped around said cylinder to force all wire segments contained in said cuts to bend in arcs upon the insertion of an electrode lead proximal termination.

32. A heart pacer in accordance with claim 27 wherein first and second ones of said plastic parts make slidable engagements with said two metallic termination blocks and said case from the sides of said case, and a third of said plastic parts is a cap which makes slidable engagement with said first and second plastic parts from above said case.

33. A heart pacer in accordance with claim 23 wherein a first of said plastic parts makes slidable engagement with said two metallic termination blocks and said case from the side of said case, and a second of said plastic parts is a cap which makes slidable engagement with said first of said plastic parts from above said case.

34. A heart pacer in accordance with claim 23 wherein first and second ones of said plastic parts make slidable engagements with said two metallic termination blocks and said case from the sides of said case, and a third of said plastic parts is a cap which makes slidable engagement with said first and second plastic parts from above said case.

35. A connector assembly for connecting at least one electrode lead proximal termination to at least two terminals extending through the case of a heart pacer; comprising at least two metallic termination blocks each for electrical connection to a respective one of said terminals; and at least two secured fluid-insulating metal-free plastic parts which make slidable engagement with each other and at least one of which makes slidable engagement with said at least two metallic termination blocks and said case; said case including a pair of upstanding capped studs, and at least one of said plastic parts including a pair of cut-outs for making locking sliding engagement with respective ones of said capped studs.

36. A connector assembly in accordance with claim 35 wherein a first of said plastic parts makes slidable engagement with said at least two metallic termination blocks and said case from the side of said case, and a second of said plastic parts is a cap which makes slidable engagement with said first of said plastic parts from above said case.

37. A connector assembly in accordance with claim 35 wherein first and second ones of said plastic parts make slidable engagements with said at least two metallic termination blocks and said case from the sides of said case, and a third of said plastic parts is a cap which makes slidable engagement with said first and second plastic parts from above said case.

* * * * *